United States Patent [19]

Raman et al.

[11] Patent Number: 5,356,635
[45] Date of Patent: Oct. 18, 1994

[54] CARBOHYDRATE GLASS MATRIX FOR THE SUSTAINED RELEASE OF A THERAPEUTIC AGENT

[75] Inventors: Siva N. Raman, St. Louis, Mo.; John P. Cunningham, Terre Haute, Ind.

[73] Assignee: Mallinckrodt Veterinary, Inc., Mundelein, Ill.

[21] Appl. No.: 91,883

[22] Filed: Jul. 13, 1993

Related U.S. Application Data

[63] Continuation of Ser. No. 802,581, Dec. 5, 1991, abandoned.

[51] Int. Cl.$^5$ .................. A61K 9/14; A61K 37/02; A61K 37/36; A61K 47/26
[52] U.S. Cl. ............................... 424/484; 424/423; 424/425; 424/426; 424/488; 424/468; 514/2; 514/772.2; 514/772.3; 514/777; 514/783; 514/786; 514/785; 514/787
[58] Field of Search ............... 424/484, 488, 425, 423

[56] References Cited

U.S. PATENT DOCUMENTS

| | | | |
|---|---|---|---|
| 2,413,419 | 12/1946 | Saunders et al. | 167/74 |
| 4,590,062 | 5/1986 | Jang | 424/19 |
| 4,671,953 | 6/1987 | Stanley et al. | 424/440 |
| 4,765,980 | 8/1988 | DePrince et al. | 424/423 |
| 4,857,506 | 8/1989 | Tyle | 514/937 |
| 5,219,572 | 6/1993 | Sivaramakrishnan et al. | 424/438 |
| 5,266,333 | 11/1993 | Cady et al. | 424/488 |

FOREIGN PATENT DOCUMENTS

| | | |
|---|---|---|
| 8904689 | 6/1989 | European Pat. Off. . |
| 0345628 | 12/1989 | European Pat. Off. . |
| 9103237 | 3/1991 | European Pat. Off. . |
| 2383659 | 10/1978 | France . |

*Primary Examiner*—Thurman K. Page
*Assistant Examiner*—James M. Spear
*Attorney, Agent, or Firm*—Wendell Ray Guffey; Barbara A. Ernst; Thomas L. Farquer

[57] ABSTRACT

A composition for the sustained release of a biologically active therapeutic agent wherein the matrix of the sustained release composition is composed of an amorphous carbohydrate glass matrix comprising a suitable carbohydrate and an agent which retards the recrystallization of the carbohydrate and a biologically active therapeutic agent and a water-insoluble wax dispersed throughout the matrix. Biologically active therapeutic agents which can be incorporated into the carbohydrate glass matrix include prolactin, growth hormones, serum albumins, growth factors or any biologically active fragment or recombinant form thereof.

20 Claims, No Drawings

CARBOHYDRATE GLASS MATRIX FOR THE SUSTAINED RELEASE OF A THERAPEUTIC AGENT

This is a continuation of application Ser. No. 07/802,581, filed Dec. 5, 1991 now abandoned.

BACKGROUND OF THE INVENTION

The present invention is directed to a novel composition of matter for the sustained release of a therapeutic agent. More specifically, the present invention relates to a composition for the sustained release of a biologically active therapeutic agent from a biodegradable, amorphous carbohydrate glass matrix. Upon administration to a mammal, the amorphous carbohydrate glass matrix slowly dissolves, releasing the biologically active therapeutic agent into the physiological fluids of the animal.

The preparation and employment of amorphous carbohydrate glasses are known in the "candy industry" as well as in the production of medicated lozenges. However, amorphous carbohydrate glasses have not been employed as matrix material for sustained release polypeptide compositions. Various sustained release methods and compositions are known for administering therapeutic agents to both humans and animals alike. U.S. Pat. No. 4,671,953, issued to Stanley et al. in 1987, describes a method and composition for administering sedatives, analgesics and anesthetics to a patient by incorporating the therapeutic agent into a lollipop. The lollipop is composed of a carbohydrate matrix or "candy matrix" with the therapeutic agent dispersed throughout the matrix. As the patient licks or sucks on the "candy matrix" the matrix breaks down, releasing the drug into the oral cavity where the drug is absorbed across the mucosal cavity. A serious limitation to this method of administering a therapeutic agent to a patient is that the therapeutic agent must be sufficiently lipophilic that it will readily pass across a mucosal membrane. Examples of therapeutic agents which can be administered by this method include morphine, fentanyl, valium, midazolam and the like. Polypeptides are not sufficiently lipophilic such that they could be administered to a patient by this means.

U.S. Pat. No. 4,765,980, issued to DePrince et al. in 1988, describes a method for stabilizing porcine growth hormone with porcine serum albumin in sustained release implant devices for swine. The porcine growth hormone and stabilizing amount of porcine serum albumin are compressed into a tablet or pellet with binders such as sodium bentonite, ethyl cellulose, stearic acid, adipic acid, fumaric acid, polyethylene glycol, deacetylated chitin and cellulose acetate. The pellets or tablets are loaded in a reservoir which can be implanted subcutaneously in swine where the growth hormone is slowly released from the reservoir. Typically, the matrix material of the reservoir is composed of polyalkylenes, polycarbonates, polyamides, modacrylic copolymers, polyesters and the like.

U.S. Pat. No. 4,857,506, issued to Tyle in 1989, describes sustained release compositions of growth hormones in multiple water-in-oil-in-water emulsions. The compositions are administered subcutaneously to an animal where the growth hormone is slowly released from the emulsion to increase the weight gain of the animal and increase milk production by a lactating animal.

U.S. Pat. No. 4,293,539, issued to Ludwig et al. in 1981, describes controlled release formulations useful in the prolonged treatment and control of microbial infections in animals. The antimicrobial agent is dispersed throughout a matrix composed of a copolymer of lactic acid and glycolic acid. The copolymeric material is polymerized without a catalyst to ensure total degradation without leaving any toxic residues. The copolymer material then is dissolved in an organic solvent and mixed with a suitable antimicrobial agent. The mixture is extruded into a desired shape and then cooled to form a hard glass-like device. Antimicrobials typically employed include penicillins, cephalosporins, tetracyclines, sulfa drugs, macrolide antibiotics and aminoglycosides.

U.S. Pat. No. 2,918,411, issued to Hill in 1959, describes a controlled release oral pharmaceutical dosage form. The essential components of the formulation include polyvinylpyrrolidone, a substantially water-insoluble agent, such as a saturated fatty acid, a saturated fatty acid ester and a pharmacologically acceptable sterol, and a pharmacologically active material. After the essential components of the formulation are mixed, the formulation is pelletized. The pellets then can be encapsulated or embodied in another type of dosage form or administered directly to a patient from the bulk pellet. Suitable pharmacologically active agents which can be employed in this sustained release composition include antibiotics, hypnotics, tranquilizing agents, antihistamines and narcotics.

Although there are a variety of sustained release compositions for many biologically active agents, there is still a need for a sustained release composition which completely degrades in the physiological fluids of the host leaving behind little, if any, residual material and which does not substantially interact with the therapeutic agent.

SUMMARY OF THE INVENTION

The present invention is directed to a sustained release composition for biologically active therapeutic agents comprising a biodegradable, amorphous carbohydrate glass matrix, a hydrophobic substance, and a biologically active therapeutic agent dispersed throughout the matrix. The composition can be administered orally to or implanted in an animal where the amorphous carbohydrate glass matrix slowly degrades, releasing a biologically active therapeutic agent into the physiological fluids of the animal.

DETAILED DESCRIPTION OF THE INVENTION

The present invention relates to a novel sustained release composition comprising a biologically active therapeutic agent dispersed throughout an amorphous carbohydrate glass matrix. More specifically, sustained release compositions of the present invention comprise a biodegradable, amorphous carbohydrate glass matrix, an agent to retard crystallization of the amorphous carbohydrate matrix, a biologically active therapeutic agent and a hydrophobic substance to modify the rate of release of the polypeptide from the amorphous carbohydrate matrix.

The composition of the present invention can be administered orally or by implanting subcutaneously such that the amorphous carbohydrate matrix slowly dissolves, releasing the therapeutic agent into the physiological fluids wherein the therapeutic agent asserts its biological activity on the animal. Advantageously, the amorphous carbohydrate matrix does not substantially interact with therapeutic agents such that the biological activity of a therapeutic agent incorporated within the matrix would be compromised. The amorphous carbohydrate glass matrix completely degrades in the physiological fluids of the host leaving very little, if any, residual material behind to be removed after release of the therapeutic agent is complete. Also advantageously, the composition has a relatively slow rate of dissolution in physiological fluids, dissolution occurs predominantly at the surface of the carbohydrate matrix, and the sustained release compositions within the scope of this invention are amenable to conventional production techniques such as extrusion, tableting and the like.

Generally, the amorphous carbohydrate component, including the recrystallization retarding agent, comprises from about 60% to about 90% by weight of the sustained release composition. The amorphous carbohydrate component comprises one or more carbohydrates mixed with an agent to retard recrystallization of the carbohydrate. Suitable carbohydrates which can be employed as matrix material include, but are not limited to, disaccharides such as sucrose, lactose, maltose or cellobiose. Suitable agents employed to retard recrystallization of the carbohydrate include, but are not limited to, polyvinylpyrrolidone (PVP), polyethylene glycols, polyvinyl alcohol, maltodextrins, sodium lauryl sulfate, oleyl alcohol, stearyl alcohol and the like. Generally, the carbohydrate component comprises from about 50% to about 80% by weight of the amorphous carbohydrate component and the recrystallization retarding agent comprises from about 10% to about 40% by weight of the amorphous carbohydrate component. Water comprises the rest of the amorphous carbohydrate component.

Therapeutic agents which can be employed in the sustained release compositions of the present invention include biologically active polypeptides, antibiotics and vitamins. As used herein, the term "polypeptide" encompasses natural and recombinant polypeptides having a desired biological activity, including bioactive polypeptides having deleted, replaced or altered amino acid sequences in comparison with the full-length natural polypeptide.

Polypeptides which can be incorporated within the amorphous carbohydrate glass matrices generally have a molecular weight of at least 1000 daltons and no more than about 200,000 daltons. The polypeptide component of the sustained release compositions of the present invention ranges from about 2% to about 20% by weight of the composition. Examples of polypeptides which can be employed to practice this invention include, but are not limited to, prolactin (PRL), serum albumin, growth factors and growth hormones, i.e., somatotropin. Serum albumins which can be employed to practice this invention include but are not limited to, bovine, ovine, equine, avian and human serum albumin. Examples of suitable growth factors include epidermal growth factor (EGF), insulin-like growth factor I (IGF-I), insulin-like growth factor II (IGF-II), fibroblast growth factor (FGF), transforming growth factor alpha (TGF-α), transforming growth factor beta (TGF-β), nerve growth factor (NGF), and platelet-derived growth factor (PDGF). Particularly preferred growth factors include recombinant human insulin-like growth factors I (rHuIGF-I) and II (rHuIGF-II). Somatotropins which can be employed to practice this invention include, but are not limited to, bovine, porcine, ovine, equine, arian and human somatotropin. A preferred porcine somatotropin is delta-7 recombinant porcine somatotropin, described and claimed in European Patent Application Publication No. 104,920 (Biogen).

Hydrophobic substances which can be employed to modify the rate of release of a therapeutic agent from an amorphous carbohydrate glass matrix include water insoluble waxes such as white beeswax, yellow beeswax, candelilla, carnauba wax, castor wax, cetyl esters wax and the like. Other materials such as cholesterol glycerol monostearate, fatty acid esters of glycerol, fatty acids such as stearic acid, fats, lipids, etc. also can be employed. Generally, these water-insoluble substances comprise from 5% to about 25% by weight of the sustained release composition.

Optionally, the formulation also may contain aciduants, preservatives, etc. known to those skilled in the art.

The sustained release compositions of the present invention can be prepared by a variety of methods. Examples of suitable methods for preparing amorphous carbohydrate glass matrices are disclosed in *Pharmaceutical Dosage Forms*, Vol. 1, chapter 8, "Medicated Lozenges" by D. Peters (H. Lieberman and L. Lachman, eds.) herein incorporated by reference. A preferred method comprises mixing an aqueous solution of a carbohydrate, wherein the carbohydrate ranges from about 60% to about 80% by weight of the solution, with an aqueous solution of a recrystallization retarding agent. Generally, a recrystallization retarding agent comprises from about 25% to about 40% by weight of the solution. The two aqueous solutions are thoroughly mixed and heated to a temperature ranging from about 110° C. to about 120° C. until the mixture becomes viscous. The viscous mixture then is allowed to cool to a temperature of from about 60° to about 70° C. A suitable biologically active therapeutic agent then is thoroughly kneaded into the viscous carbohydrate composition using any suitable technique, such as by hand. A water insoluble substance as described above also can be added and kneaded into the viscous carbohydrate-therapeutic agent mixture.

The resulting mixture can be extruded through preheated syringes at temperatures ranging from about 60° to about 70° C. to form rods. The viscous carbohydrate-therapeutic agent mixture also can be shaped into tablets and the like according to methods practiced in the art. The shaped carbohydrate-therapeutic agent mixture is allowed to cool to room temperature (i.e., about 18°–25° C.), thus forming a sustained release composition comprising an amorphous carbohydrate glass matrix having a biologically active therapeutic agent dispersed throughout the matrix. Sustained release compositions within the scope of this invention can be implanted subcutaneously in an animal where the amorphous carbohydrate glass matrix slowly erodes, releasing a biologically active therapeutic agent into the physiological fluids of the host. Other modes of administration, such as oral dosing, also can be employed.

The following examples are intended to particularly point out and more clearly illustrate the invention and are not intended to be limiting.

EXAMPLE 1

An aqueous sucrose solution (70% by weight, 24.11 g) was mixed with an aqueous solution of polyvinylpyrrolidone (PVP) (33% by weight, 34.10 g) and heated to about 115°–118° C. As the water in the mixture continued to evaporate, the mixture became viscous and turned pale yellow to deep amber in color. The hot viscous mixture was poured into a beaker and cooled to room temperature (about 20° C.) yielding a solid amorphous sucrose matrix (ASM). The X-ray diffraction pattern, determined using a Philips 3100 X-ray Powder Diffractometer, indicated an amorphous structure. The water content of the ASM was about 11.8% by weight and the reducing sugar content was about 1.4%. The water content was determined using the commonly known Karl Fischer Moisture Determination method. The amount of reducing sugar was determined by the reduction of alkaline ferricyanide and subsequent calorimetric analysis at 410 nm.

EXAMPLE 2

ASM (1.5 g) as prepared in Example 1 was placed on a Teflon ® sheet preheated to about 60° to 70° C. and thoroughly kneaded with 0.15 g of solid particles of bovine serum albumin (BSA) (obtained from Sigma Chemical Co.) Molten beeswax (0.302 g) was added to the BSA-ASM mixture and kneaded to give Formulation A comprising: ASM (77 parts), BSA (8 parts) and beeswax (15 parts). The resulting viscous formulation was heated to about 70° C. and loaded into pre-heated plastic syringes also at about 70° C. The formulation was extruded to give cylindrical rods. Short sections of about 5 mm in length were cut from these rods to give 6 cylindrical pieces weighing 110–135 mg. Each cylindrical rod was placed in a culture tube containing 5 ml of 10mM phosphate buffered saline (PBS) at a pH of 7.4. The cylindrical pieces were shaken in a Gyrotory ® water-bath at 37° C. Periodically, the solutions were removed and replaced with fresh PBS. BSA concentrations in the buffer solutions were determined by measuring the UV absorbances at 278 nm with a Beckman spectrophotometer (Model DU-70). Release profiles were constructed by calculating the cumulative percent of BSA released at various time intervals. Table 1 discloses the mean values of the cumulative percent of BSA released at different time periods.

TABLE 1

| Time | Release of BSA from Formulation A | |
|---|---|---|
| | Cumulative % of BSA Released | |
| Days | Mean | Standard Deviation |
| 0.083 | 22.0 | 4.6 |
| 0.33 | 32.7 | 8.0 |
| 1.0 | 45.5 | 10.9 |
| 2.0 | 55.4 | 11.8 |
| 3.0 | 61.9 | 12.0 |
| 4.0 | 66.6 | 11.8 |
| 5.0 | 70.6 | 11.6 |

The pattern of release of BSA shows that an amorphous carbohydrate glass matrix can be employed for the sustained release of a polypeptide.

EXAMPLES 3 TO 5

Formulations B, C and D were prepared according to the methods described in Examples 1 and 2 above except that the amount of beeswax in each formulation differed. Formulation A in Example 2 comprised 15 parts by weight of beeswax while Formulations B, C and D comprised 8.3, 4.4 and 0 parts by weight of beeswax, respectively. The release rates were determined by the same method as in Example 2. The compositions of Formulations B, C and D were as follows:

| Formulation B | |
|---|---|
| Component | Amount |
| ASM | 1.50 g (83.3 parts) |
| BSA | 0.15 g (8.3 parts) |
| Beeswax | 0.15 g (8.3 parts) |

The release of BSA from the cylinders was complete in about 3.5 hours.

| Formulation C | |
|---|---|
| Component | Amount |
| ASM | 1.50 g (87 parts) |
| BSA | 0.15 g (8.7 parts) |
| Beeswax | 0.075 g (4.4 parts) |

The release of BSA from the cylinders was complete in about 1.75 hours.

| Formulation D | |
|---|---|
| Component | Amount |
| ASM | 1.50 g (91 parts) |
| BSA | 0.150 g (9 parts) |
| Beeswax | 0.00 g |

The release of BSA from the cylindrical pieces was complete in about 1 hour.

The results from this experiment indicate that the release rate of a polypeptide from an amorphous carbohydrate glass matrix can be modified by varying the amount of wax in the sustained release composition. The higher the wax content in the formulation, the slower was the release of BSA.

EXAMPLES 6 AND 7

Formulation E and F were prepared according to the methods of Examples 1 and 2 except that a zinc complex of recombinant porcine somatotropin (ZnrpST) (prepared by Pitman-Moore, lot #148/010/011-820) replaced the BSA as the polypeptide in the sustained release composition. The formulation of composition E was as follows:

| Formulation E | |
|---|---|
| Component | Amount |
| ZnrpST | 0.15 g |
| ASM | 1.50 g |
| Beeswax | 0.30 g |

TABLE 2

| Time | Release of ZnrpST from Formulation E | |
|---|---|---|
| | Cumulative % of ZnrpST Released | |
| Days | Mean | Standard Deviation |
| 0.33 | 16.8 | 3.9 |
| 1.0 | 22.2 | 4.8 |
| 2.0 | 25.2 | 4.4 |
| 3.0 | 27.1 | 3.8 |

| Formulation F | |
|---|---|
| Component | Amount |
| ASM | 1.50 g |

-continued

| Formulation F | |
|---|---|
| Component | Amount |
| ZnrpST | 0.15 g |

Release of ZnrpST from Formulation F was complete in about 1 hour. The beeswax incorporated into Formulation E clearly reduced the rate of release of ZnrpST from the carbohydrate matrix, since by the third day only 27.1% of the ZnrpST had been released. This experiment clearly showed that a carbohydrate glass matrix can be employed for the sustained release of a somatotropin.

In order to find out whether the formulation techniques had affected the biological activity of the pST, radioreceptor binding assays were performed on samples of porcine somatotropin (pST) extracted from Formulation E. PST extracted from Formulation E had about 87% of the binding activity of the protein prior to formulation. The results indicated that the pST retained its activity substantially in the course of the formulation steps.

We claim:

1. A sustained release composition comprising an amorphous carbohydrate glass matrix, a biologically active therapeutic agent and a hydrophobic substance, where the carbohydrate glass matrix comprises a carbohydrate and an agent which retards recrystallization of the carbohydrate glass matrix.

2. A method of administering a biologically active therapeutic agent to a mammal comprising implanting a sustained release composition subcutaneously into said mammal wherein the composition comprises an amorphous glass carbohydrate matrix, a biologically active therapeutic agent and a hydrophobic substance, where the carbohydrate glass matrix comprises a carbohydrate and an agent which retards recrystallization of the carbohydrate glass matrix.

3. A sustained release composition according to claim 1, wherein the amorphous carbohydrate matrix comprises from about 50%–75% by weight of the matrix and the recrystallization retarding agent comprises from about 15%–40% by weight of the matrix.

4. A sustained release composition according to claim 1, wherein the hydrophobic substance is a wax.

5. A sustained release composition according to claim 4, wherein the wax comprises white beeswax, yellow beeswax, candelilla wax, carnauba wax, vegetable waxes, castor wax or cetyl esters wax.

6. A sustained release composition according to claim 1, wherein the hydrophobic substance comprises cholesterol, fatty acid esters or fatty acids.

7. A sustained release composition according to claim 1, wherein the hydrophobic substance comprises from about 5% to about 25% by weight of the composition.

8. A sustained release composition according to claim 1, wherein the carbohydrate comprises sucrose, lactose, maltose or cellobiose.

9. A sustained release composition according to claim 1, wherein the amorphous carbohydrate matrix comprises from about 60% by weight to about 90% by weight of the sustained release composition.

10. A sustained release composition according to claim 1, wherein the therapeutic agent comprises a polypeptide, vitamin or antibiotic.

11. A sustained release composition according to claim 10, wherein the polypeptide comprises prolactin, serum albumins, somatotropins, growth factors or any biologically active fragment or recombinant form thereof.

12. A sustained release composition according to claim 11, wherein the therapeutic agent comprises from about 2% to about 20% by weight of the composition.

13. A sustained release composition of claim 11, wherein the serum albumin comprises bovine, ovine, porcine, avian or human serum albumin.

14. A sustained release composition according to claim 11, wherein the somatotropin comprises bovine, ovine, porcine, arian or human somatotropin.

15. A sustained release composition according to claim 11, wherein the growth factor comprises epidermal growth factor, insulin-like growth factor I, insulin-like growth factor II, fibroblast growth factor, transforming growth factor alpha, transforming growth factor beta, platelet-derived growth factor or nerve growth factor.

16. A sustained release composition according to claim 1, wherein the recrystallization retarding agent comprises polyvinylpyrrolidone, polyvinyl alcohol, polyethylene glycols, maltodextrins, sodium lauryl sulfate, oleyl alcohol or stearyl alcohol.

17. A sustained release composition according to claim 1, wherein the amorphous carbohydrate glass matrix comprises from about 60%–90% by weight of the composition; the biologically active therapeutic agent comprises from about 2%–20% by weight of the composition; and the wax comprises from about 5% to about 25% by weight of the composition.

18. A sustained release composition comprising a mixture of recombinant porcine somatotropin; polyvinylpyrrolidone, and beeswax dispersed in an amorphous sucrose glass matrix.

19. A method for preparing a sustained release composition comprising:
   a. Mixing an aqueous sucrose solution with an aqueous solution of polyvinylpyrrolidone;
   b. heating the mixture at a temperature of from about 115° C. to about 118° C. to evaporate a sufficient amount of water such that the mixture becomes viscous;
   c. cooling the viscous mixture to a temperature of from about 60° C. to about 70° C.;
   d. kneading a zinc complex of recombinant porcine somatotropin and beeswax with the viscous mixture of sucrose and polyvinylpyrrolidone;
   e. extruding the viscous mixture of sucrose, polyvinylpyrrolidone, beeswax and somatotropin to form rods;
   f. cutting the rods to form short cylindrical sections; and
   g. cooling the short cylindrical sections to form sustained release cylinders having an amorphous sucrose and polyvinylpyrrolidone glass matrix and somatotropin and beeswax dispersed throughout the matrix.

20. A method of administering a biologically active therapeutic agent to a mammal comprising orally administering a sustained release composition to the mammal where the composition comprises an amorphous carbohydrate glass matrix, a biologically active therapeutic agent and a hydrophobic substance, where the carbohydrate glass matrix comprises a carbohydrate and an agent which retards recrystallization of the carbohydrate glass matrix.

* * * * *